United States Patent [19]

Pestes

[11] Patent Number: 4,720,017
[45] Date of Patent: Jan. 19, 1988

[54] SPECIMEN KITS AND STOPPER THEREFOR

[75] Inventor: Cornelius N. Pestes, Boring, Oreg.

[73] Assignee: Medical Media Laboratory, Inc., Boring, Oreg.

[21] Appl. No.: 402,370

[22] Filed: Jul. 27, 1982

[51] Int. Cl.[4] .............................................. B65D 55/02
[52] U.S. Cl. ................................... 215/227; 206/210; 206/438; 206/569
[58] Field of Search .................... 128/749, 756, 759; 604/1, 2, 3; 206/210, 438, 568, 569; 215/227, 228

[56] References Cited

U.S. PATENT DOCUMENTS

| | | | |
|---|---|---|---|
| 2,510,490 | 6/1950 | Ager | 604/1 |
| 2,803,028 | 8/1957 | Flynn | 215/228 |
| 2,849,141 | 8/1958 | Abbiati et al. | 215/228 |
| 3,004,681 | 10/1961 | Jinkens et al. | 215/228 |
| 3,164,279 | 1/1965 | Towns | 215/227 |
| 3,189,169 | 7/1965 | Davidson | 215/228 |
| 3,262,596 | 7/1966 | Zillmann | 215/227 |
| 3,783,106 | 1/1974 | Henshilwood | 128/759 |
| 3,842,790 | 10/1974 | Clark | 215/228 |
| 3,870,186 | 3/1975 | Reinhard | 215/228 |
| 3,890,204 | 6/1975 | Auery | 128/759 |
| 3,938,898 | 2/1976 | Reitknecht | 604/2 |
| 3,945,617 | 3/1976 | Callery | 215/100 R |
| 4,175,608 | 11/1979 | White | 128/759 |
| 4,194,848 | 3/1980 | Kingsford | 215/228 |

Primary Examiner—Stephen Marcus
Assistant Examiner—David T. Fidei
Attorney, Agent, or Firm—Jack E. Day

[57] ABSTRACT

An improvement in specimen kits that reduces significantly the possibility of contamination of the specimen by either user or container; of the patient by the swab used to obtain the specimen; and of a subsequent handler of the container by the specimen. It permits the collected specimen to be transported to the diagnostic processing laboratory in common, widely used medical specimen mailing containers, while permitting the use of swab lengths that are appropriate to the type of specimen desired. The improvement is made possible by a unique double-ended stopper that maintains the specimen container sterile until use, then acts as a cap for engaging the swab shaft for withdrawal while maintaining a tight and sterile shipping container after the specimen is taken and while it is subsequently handled.

16 Claims, 3 Drawing Figures

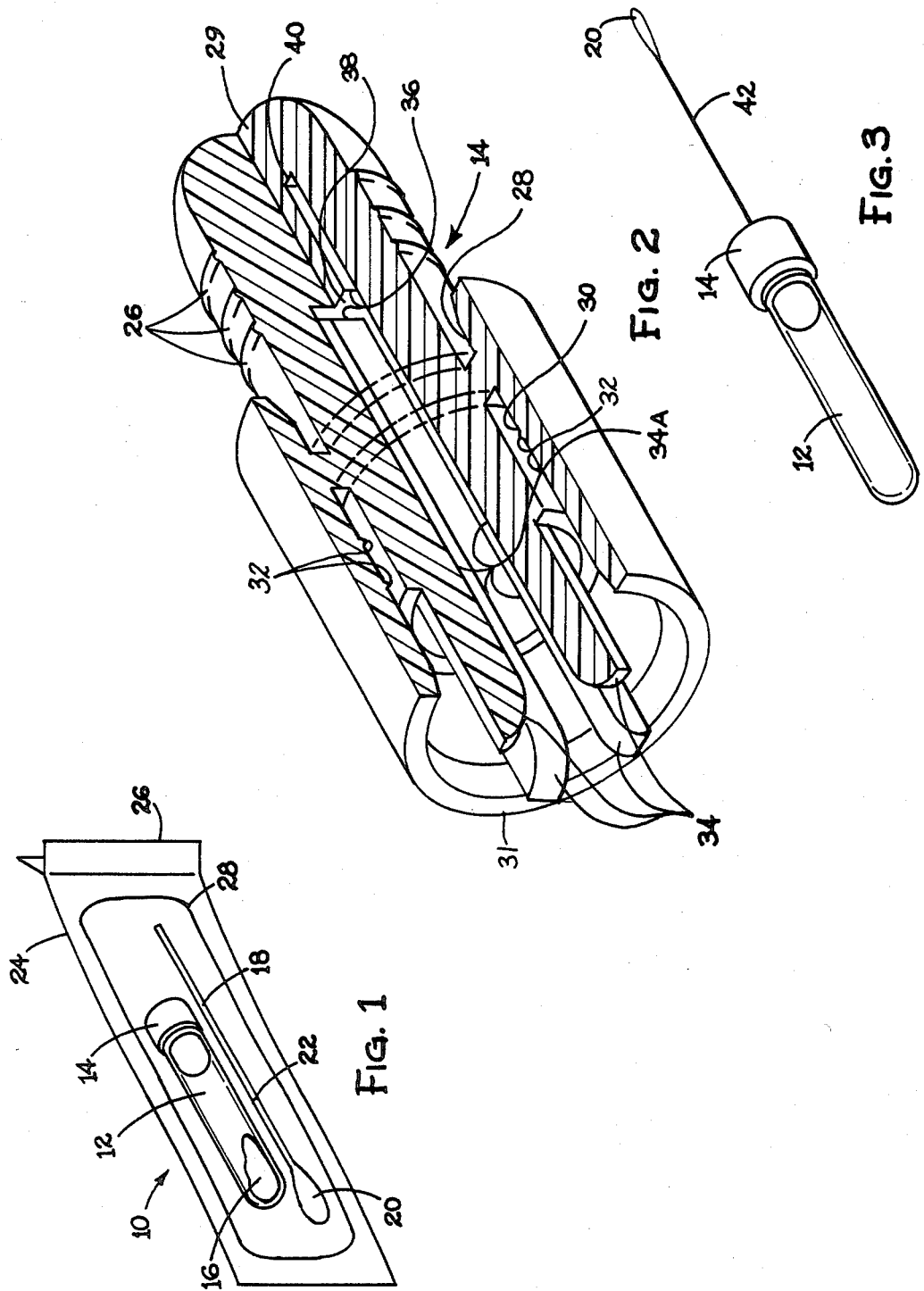

SPECIMEN KITS AND STOPPER THEREFOR

BACKGROUND OF THE INVENTION

This invention relates to improvements in kits for taking specimens and safeguarding them during transport to a diagnostic laboratory. More particularly, this invention relates to a unique stopper which enables the above activity to be conducted more efficiently, safely and surely.

In the past, the taking of samples of all kinds for analysis has been attended with several problems. For example, there is always the danger of contaminating the samples, or being contaminated by them. Especially is this true with the taking of samples for medical analysis and diagnosis, where the problems are three-fold: that of infecting the patient with a contaminated swab; that of contaminating the sample or specimen with contaminated swabs or containers; and that of infecting a subsequent handler of the specimen by a contaminated swab or container. In addition to the above problems, there is also the problem of having swab-shafts of sufficient length to obtain deep samples from the various orifices of the body. Further, it is desirable that the sample or specimen container fit in standard medical mailing containers, such as that manufactured under the tradename METPATH, to take advantage of favorable mailing or shipping rates and handling.

Specimen kits are available from several sources, packaged in sterilized plastic containers and containing a tube of any of several types with an appropriate one of several types of culture medium therein to maintain the specimens alive during transport to the analysis and diagnostic laboratory. One such kit features a swab located at one end of a metal or plastic shaft, the other end of which is affixed into an extruded plastic tube sealed at one end around the swab shaft to form a cap. This cap fits snugly over another, lengthier plastic tube, the lower end of which is sealed and which, with a second seal forming a small pocket, contains a small amount of a culture medium. In use, the shaft is withdrawn from its protective tube, is used to obtain a specimen, and is re-inserted into the protective tube. The seal into the culture medium is broken by pinching the ends toward one another, and the specimen is inserted into the medium, where it rests during shipment to the diagnostic processing laboratory. The shipping length of the used kit containing the speciment is about 6.5", which is too large for the standard medical shipping container. The effective length of the swab shaft—that is, the depth to which it can penetrate a body orifice without the cap touching surrounding tissue and thereby becoming contaminated—is less than 3.4". In addition to the possibility of the cap becoming contaminated and thus posing a danger of infection to subsequent handlers, the protective tube is deformable, with the possibility of an opening developing which would permit the culture medium to dry out, thereby destroying the specimen. A significant proportion of specimens are lost in that manner with this particular kit.

Another specimen kit in wide use uses a plastic shaft upon which to mount the swab material, and uses a molded plastic cap which is not subject to deformation and the drying out of the culture medium and subsequent loss of the specimen. The bottom end of the plastic tube which holds the swab prior to use contains a small amount of culture medium, and the swab is held about 0.5"–0.75" above the medium before use. The cap is sealed to the plastic tube with a tamper evident seal to insure sterility. In use, the cap is twisted to break the seal, the swab is withdrawn and is used to obtain the specimen, and is re-inserted into the tube and into the culture medium. The shipping length of the used kit containing the specimen is about 6.2", while the effective length of the swab is about 3.4".

Yet a third specimen kit contains a plastic shaft with one end molded into a cap, and a swab mounted on the other end. The lower end of the tube which contains the swab before use has a glass ampule containing a solution to keep the specimen alive. In use, the swab is withdrawn, the speciment obtained, and the swab is reinserted into the protective tube. The glass ampule is broken by squeezing it, and the swab is pushed into contact with a moistened pledget. The cap of the tube contains a molded in, circumferential ring to provide a seal to prevent the solution from drying out. The shipping length of the used kit is 7.4", and the effective length of the swab shaft is about 4.0".

Other speciment kits are available which have more-or-less the same characteristics as those described above. In addition to the short effective length of the swab shaft, they have excessive length to be shipped in the standard mailing container, which provide space for several specimen containers ranging in length from 3" to 5.0". In addition, those kits which use the cap for a handle suffer from the defect that the cap obstructs the physician's view when he is taking samples at the extreme effective length of the shaft.

In summary, the specimen kits used in the past have problems in maintaining airtight seals to avoid drying out the culture medium and destroying the specimen; in obtaining specimens from substantial depth without contaminating the cap, with the danger of infecting subsequent handlers; of having a shipping length after use greater than the spaces available in standard mailing containers; and in having the cap, which acts as a handle, obstruct the physician's view when obtaining specimens at the extreme length of the swab shaft.

SUMMARY OF THE PRESENT INVENTION

The present invention offers a safe, efficient, convenient and economical way to obtain specimens and transport them to an analytical and diagnostic laboratory, while overcoming the aforementioned shortcomings and providing additional features hereinafter to be described.

The present invention provides a unique, double-ended stopper having a male end and a female end, hereinafter to be described, for a specimen container which is a part of a specimen kit such as has been described hereinbefore. The specimen kit contains a plastic or metallic shaft with a swab mounted thereon which is not limited in effective length, as are the kits hereinbefore described. The swab is sealed into a sterile package with a specimen container closed by the aforementioned unique stopper. In use, the package is opened, the swab shaft withdrawn, and the specimen is taken, more-or-less as described above for conventional specimen kits. However, since the swab shaft does not have a cap mounted or molded thereon, there is nothing to be contaminated on its exterior when a deep specimen is sought at the limits of the shaft length. Even if the outer end of the shaft comes into contact with tissue surrounding the cavity from which a specimen is sought, this portion of the shaft is discarded during subsequent handling. When the swab with the specimen thereon is withdrawn from the cavity, the unique stopper hereinbefore mentioned is withdrawn from the specimen tube and the swab is inserted about ¾ of the way into the specimen tube, whereupon it is broken off at a prescored point on the shaft by bending it against the side of the specimen tube and the excess length discarded. The unique stopper is inverted and the female end, with a special gripping means therein, hereinafter described, is placed over the protruding end of the broken shaft. As the stopper is pressed onto the mouth of the specimen tube, the broken end of the shaft is forced firmly into the gripping means, and the swab with the specimen thereon in forced into the culture medium. The specimen is nourished by the culture medium during transport to the diagnostic processing laboratory, the specimen container is tightly sealed which prevents dryout of the culture medium and destruction of the specimen, and the gripping means holds the shaft sufficiently tight to enable the swab to be withdrawn at the processing laboratory. In addition, the female end of the stopper covers the end of the specimen tube so that, in case the rim around the mouth of the specimen tube has become contaminated during insertion of the swab with the specimen thereon, a subsequent handler cannot come in contact with said contaminated portion and thereby become infected. This unique feature of the invention is accomplished by providing overlapping annular lips on the stopper, extended axially, so that the rim around the mouth of the specimen tube is covered both before and after use, as hereinafter more completely described. The overlapping annular lip on the male end of the stopper prevents the rim of the mouth of the specimen tube from becoming contaminated prior to use by accidental contact, and the aforedescribed overlapping annular lip of the female end of the stopper prevents a subsequent handler from coming into contact with any contamination accidentally deposited on the rim of the mouth of the specimen tube.

The aforementioned gripping means enables the swab shaft to be shortened after use and thereupon affixed to the stopper for subsequent handling, providing a convenient, simple and safe way to obtain deep specimens while at the same time having a specimen kit which can be shipped in standard medical mailing containers.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is a general view of a specimen kit embodying the elements of the invention.

FIG. 2 is a detailed cut-away view of the double-ended stopper of the invention, depicting the various features thereof.

FIG. 3 is a general view showing an alternate embodiment of the invention.

DETAILED DESCRIPTION OF THE PREFERRED EMBODIMENT

Turning now to FIG. 1, we see at 10 a medical specimen kit which embodies the invention. A specimen tube 12 is capped by a double-ended stopper 14, hereinafter described in greater detail. The specimen tube 12 contains a quantity of a culture medium 16 in the lower end. Also included in the kit 10 is a shaft 18 tipped with an absorbent material forming a swab 20 for obtaining specimens thereon. The shaft 18 is scored as indicated at 22, for a purpose hereinafter described. The specimen tube 12 and the swab shaft 18 are contained in a package of a type well known in the art, composed of a relatively stiff backing material 24 which is fronted by a clear flexible film 26 periphally sealed around the edges to backing material 24 as indicated by 28, so that an air and moisture-proof package is obtained. The package and its contents can be sterilized by any of several well known processes, including but not restricted to gamma radiation. The stiff backing material 24 and the more flexible film 26 can have instructions or other information printed on them if desired.

In use, the tab of flexible material 26 is pulled from the backing material 24, breaking the seal 28 and exposing the end of the swab shaft 18 and the double-ended ended stopper 14, which has the male 29 end pressed into the specimen tube 12. The swab shaft 18 is withdrawn and is used to obtain a desired specimen. Since the shaft 18 is shortened in a subsequent operation, hereinafter described, it can be supplied in any length that is appropriate for for the specimen involved. The double-ended stopper 14 is then withdrawn from the specimen tube 12, and the swab shaft 18 is inserted about ¾ of the depth of the tube 12 and bent sharply, whereupon it breaks at the pre-scored line 22, and the broken-off portion of the shaft is discarded, eliminating the possibility of infection from that source for subsequent handlers. The remaining length of the swab shaft 18 in the specimen tube 12 is appropriate for the next operation to be performed, as now described. The double-ended stopper 14 is inverted and the female 31 end, with gripping means 34 incorporated within, as seen more clearly in FIG. 2 and hereinafter more completely described, is pressed onto the broken end of the shaft 18, which presses the swab 20 into the culture medium to preserve it until it can be processed at an analytical, diagnostic laboratory. The swab end of the shaft 18 encounters the closed end of the specimen tube 12, whereupon the gripping means 34 will continue to be pressed onto the broken end of the shaft 18 until it encounters the stop 38, also seen in FIG. 2. At the same time as the gripping means 34 has been pushed onto the shaft 18, the female end 31 of the stopper 14 has been pushed over the rim of the open end of the specimen tube 12, effectively sealing it. Any contamination of the rim which might have occurred during insertion of the swab 20 will be covered by the annular overlapping lip 30 of the stopper 14, further reducing the danger of infection for subsequent handlers of the specimen tube 12.

FIG. 2 depicts more clearly the details of the double-ended stopper 14, which incorporates a male end 29 and a female end 31. The male 29 end 24 of the stopper 14 is the portion of the stopper originally inserted in the specimen tube 12 when it is initially presented to the user upon opening of the sealed sterile container. It has one or more circumferential rings 26 molded onto its surface to provide an airtight seal when it is inserted in the specimen tube 12, thus preventing leakage of air or the drying out of the culture medium 16 before use. This end of the stopper 14 also incorporates an annular overlapping lip 28 which fits over the rim of the specimen tube 12, preventing it from being contaminated with a foreign substance prior to use.

The female end 31 of the stopper 14 is the end that is placed over the rim of the opening of the specimen tube 12 after a specimen has been obtained on the swab 20 and has been inserted therein and broken off. This female end 31 of the stopper 14 contains several features which will be described individually, since they are important aspects of the present invention. As stated before, this end 31 of the stopper contains therein a gripping means 34, which can be any of several well-known designs but is preferably embodied as fingers 34. These fingers 34 are extended axially from the inside of the base of the stopper, and are designed with tapering inner surface 34A so that they will exert a greater and greater pressure on the shaft 18 as the stopper 14 is pushed thereunto. This feature creates a stable and usable grip when it is necessary at the diagnostic processing laboratory to withdraw the swab 20 from the specimen tube 12 and smear the specimen onto culture plates. However, if further processing requires that the swab be left in another receptacle, it is necessary only to force the swab shaft 18 against the side of said other receptacle and bend the stopper 14 against the resistance thereof, and the gripping fingers 34 will resiliently release the shaft 18.

The deep annular overlapping lip 30 is designed to fit over the rim of the opening of the specimen tube 12 after a specimen has been inserted therein, to protect a subsequent handler from the danger of being infected by accidental contact with contamination which might have been deposited thereon when the specimen was inserted. The deep annular overlapping lip 30 preferably has one or more circumferential rings 32 molded onto its inner surface to provide an airtight seal to prevent the destruction of a specimen by drying out of the culture medium.

An exemplary further use of the stopper 14 is illustrated in FIG. 3. In the case of a male suspected of having contracted gonorrhea, specimens for diagnosis are usually obtained from the urethral canal, and the plastic shaft 18 described in the foregoing embodiment could possibly cause discomfort during insertion therein because of its relatively large size. Consequently, a thin swab shaft 42, fabricated for example of a thin metallic wire with an absorbent material forming a swab 20 on the end thereof, may be used. The cavities 40 of FIG. 2, located on either side of the web 36 connecting two opposing fingers 34, are designed specifically to accept wire 42 of the size normally used for such purposes, the wire being slightly larger than the width of the cavity 40 so that it is resiliently gripped by the plastic of the stopper 14. Such a use does not require the long shaft 18 of the earlier described swab 20, and can be packaged already inserted in the stopper 14, of a correct length to be fully inserted into the specimen tube 12 without shortening, as is necessary with the longer shaft 18.

The specimen tube 12, with either the shortened longer shaft 18 or the shorter, smaller diameter shaft 42 inserted therein and capped with the stopper 14, is of a proper length to be contained in a standard medical mailing container such as is usually encountered in the trade.

It should be emphasized that, although the above detailed description has been in terms of medical specimen kits, it is expressly intended to be used for specimens of any kind where there is a substantial possibility of contamination of specimens or users. Thus, it could be used to collect chemical, geological, biological or any other type of specimen where there is a desire to avoid contamination of the specimen by the user, of the user by the specimen, or to avoid contamination of the specimen tube by foreign substances. The kit and the unique stopper therefor will be appropriate for collection and safeguarding of specimens under widely varying conditions, and the lack of mention of such conditions is not meant to exclude them from being covered hereby. The terms and expressions which have been employed in the foregoing specification are used therein as terms of description and not as terms of limitation, and there is no intention, in the use of such terms and expressions, of excluding equivalents of the features shown and described, or portions thereof, it being recognized that the scope of the invention is defined and limited only by the claims which follow:

What I claim as my invention is:

1. A specimen kit for providing non-contaminating storage for a specimen, including a container having an opening and having a rim surrounding said opening, a shaft having absorbent material at one end thereof for collecting said specimen thereon, said specimen being inserted in said opening on said shaft, a stopper for said container, said stopper for maintaining said container sterile internally prior to insertion of said specimen therein, the improvement comprising:
   (a) said stopper having:
      (1) a first end and a second end, said first end being inserted in said opening before use;
      (2) an annular ring joined to said stopper at a junction between said first end and said second end, said annular ring extending axially from said junction toward said first end and said second end;
      (3) gripping means associated with said second end;
   (b) said stopper being withdrawn from said opening and inverted prior to insertion of said specimen therein;
   (c) said shaft being breakable at a preselected point following insertion in said opening; and
   (d) said gripping means engaging said breakable shaft when said second end is pressed upon said rim.

2. The specimen kit of claim 1 wherein said gripping means comprises at least three fingers extending axially from said junction toward said second end and arranged radially and grippingly around said shaft.

3. The specimen kit of claim 1 wherein said first end has a circumferential ridge thereon.

4. The specimen kit of claim 1 wherein said second end has an internal circumferential ridge therein.

5. The specimen kit of claim 1 wherein said first end has a circumferential ridge thereon and said second end has an internal circumferential ridge therein.

6. A specimen kit for providing noncontaminating storage for a specimen, including a container having an opening and having a rim surrounding said opening, a shaft having absorbent material at one end thereof for collecting said specimen thereon, said specimen being inserted in said opening on said shaft, a stopper for maintaining said container sterile internally prior to insertion of said speciment therein, the improvement comprising:
   (a) said stopper having:
      (1) a first end and a second end, said first end being inserted in said opening before use;
      (2) an annular ring joined to said stopper at a junction between said first end and said second end, said annular ring extending axially from said junction toward said first end and said second end;
      (3) gripping means associated with said second end;

(b) said shaft being inserted in said gripping means; and (c) said stopper being withdrawn from said opening prior to collection of said specimen and inverted prior to insertion of said specimen in said opening.

7. The specimen kit of claim 6 wherein said gripping means is contained internally to said second end.

8. The specimen kit of claim 6 wherein said gripping means is a cavity contained internally to to said junction.

9. The specimen kit of claim 6 wherein said first end has a circumferential ridge thereon.

10. The specimen kit of claim 6 wherein said second end has an internal circumferential ridge therein.

11. The specimen kit of claim 6 wherein said first end has a circumferential ridge thereon and said second end has a circumferential ridge therein.

12. A stopper for a speciment container, said container having an opening therein and having a rim surrounding said opening, said stopper comprising:

(a) a first end for insertion into said opening;

(b) a second end for insertion into said opening, said second end being joined to said first end at a junction;

(c) an annular ring joined to said stopper at said junction, said annular ring extending axially away from said junction toward said first end and toward said second end;

(d) said annular ring fitting over said rim when said first end or said second end is inserted into said opening; and (e) gripping means associated with said second end, said gripping means engaging a shaft when said second end is inserted into said opening.

13. The stopper of claim 12 wherein said gripping means comprises at least three fingers extending axially from said junction toward said second end and arranged radially and grippingly around said shaft.

14. The stopper of claim 12 wherein said first end has a circumferential ridge thereon.

15. The stopper of claim 12 wherein said second end has an internal circumferential ridge therein.

16. The stopper of claim 12 wherein said first end has a circumferential ridge thereon and said second end has an internal circumferential ridge therein.

* * * * *